United States Patent [19]

Wehner et al.

[11] 4,052,426
[45] Oct. 4, 1977

[54] PROCESS FOR THE MANUFACTURE OF DIMETHYL-TIN DICHLORIDE

[75] Inventors: Wolfgang Wehner, Zwingenberg; Rudolf Maul, Lorsch, Hessen; Hans-Wolf Jung, Burgdorf-Ehlershausen, all of Germany

[73] Assignee: Ciba-Geigy Corporation, Ardsley, N.Y.

[21] Appl. No.: 659,865

[22] Filed: Feb. 20, 1976

Related U.S. Application Data

[63] Continuation-in-part of Ser. No. 509,886, Sept. 27, 1974, abandoned.

[30] Foreign Application Priority Data

Oct. 1, 1973 Switzerland .................. 14031/73

[51] Int. Cl.$^2$ .............................................. C07F 7/22
[52] U.S. Cl. ................................................ 260/429.7
[58] Field of Search ..................................... 260/429.7

[56] References Cited

U.S. PATENT DOCUMENTS

| | | | |
|---|---|---|---|
| 3,414,595 | 12/1968 | Oakes ................................ | 260/429.7 |
| 3,901,824 | 8/1975 | Knezevic et al. ................. | 260/429.7 |
| 3,970,679 | 7/1976 | Jung et al. ........................ | 260/429.7 |

OTHER PUBLICATIONS

Chemical Abstracts v80, 83247m (1974).

*Primary Examiner*—Helen M. S. Sneed
*Attorney, Agent, or Firm*—Luther A. R. Hall

[57] ABSTRACT

Complexes composed of alkylphosphines or of alkylphosphonium chlorides and tin tetrachloride are good catalysts for the preparation of dimethyl-tin dichloride from tin and methyl chloride in the presence of sulphones and carbonates as solvents.

8 Claims, No Drawings

PROCESS FOR THE MANUFACTURE OF DIMETHYL-TIN DICHLORIDE

This application is a continuation-in-part application of parent application Ser. No. 509,886, filed Sept. 27, 1974 now abandoned.

The invention relates to compounds of the formula $$[R_3P(R'Cl)_a]SnCl_4 \qquad (I)$$

in which R is a straight-chain or branched alkyl group having 1 to 18 C atoms, R' has the same meaning as R or is a Cl atom and $a$ has the value 0 or 1, and to their use in the preparation of dimethyl-tin dichloride from metallic tin or tin alloys by means of methyl chloride according to the equation $$2CH_3Cl + Sn \rightarrow (CH_3)_2SnCl_2 \qquad (1)$$

at 100° to 300° and a pressure of 0 to 150 atmospheres gauge, characterized in that the reaction is carried out in the presence of at least one compound of the formula I.

In formula I, R is preferably a straight-chain or branched alkyl group having 1 to 12, particularly 1 to 8, C atoms and R' preferably has the same means as R or denotes a Cl atom. Compounds which are particularly preferred are those of the formulae

[(C$_4$H$_9$)$_3$P]SnCl$_4$, [(C$_8$H$_{17}$)$_3$P]SnCl$_4$, [(C$_4$H$_9$)$_4$PCl]SnCl$_4$,
[(i-C$_3$H$_7$)$_3$CH$_3$PCl]SnCl$_4$, [(C$_4$H$_9$)$_3$CH$_3$PCl]SnCl$_4$,
[(C$_4$H$_9$)$_3$C$_8$H$_{17}$PCl]SnCl$_4$, [(C$_4$H$_9$)$_3$C$_{12}$H$_{25}$PCl]SnCl$_4$,
[(C$_4$H$_9$)$_3$C$_{18}$H$_{37}$PCl]SnCl$_4$, [(C$_8$H$_{17}$)$_3$CH$_3$PCl]SnCl$_4$,
[(C$_8$H$_{17}$)$_3$C$_2$H$_5$PCl]SnCl$_4$, [(C$_4$H$_9$)$_3$PCl$_2$]SnCl$_4$ and
[(C$_8$H$_{17}$)$_3$PCl$_2$]SnCl$_4$.

The compounds of the formula I in which R, R' and $a$ have the meaning indicated, are good catalysts and co-catalysts, for example for polymerisations and poly-condensations and for the preparation of organo-elementary compounds. Their biocidal properties offer further possibilities for use, such as, for example, as herbicides.

In order to prepare the compounds according to the invention, phosphane compounds are reacted with tin-(IV) chloride with or without a solvent at temperatures of 20° to 150° C:

$$R_3P + SnCl_4 \rightarrow [R_3P]SnCl_4 \qquad (2)$$

$$R_3P + 2SnCl_4 \rightarrow [R_3PCl_2]SnCl_4 + SnCl_2 \qquad (3)$$

$$R_3PR'Cl + SnCl_4 \rightarrow [R_3PR'Cl]SnCl_4 \qquad (4)$$

A further subject of the present invention is, therefore, a process for the manufacture of compounds of the formula I $$[R_3P(R'Cl)_a]SnCl_4 \qquad (I)$$

wherein R is a straight-chain or branched alkyl group having 1 to 18 C atoms, R' has the same meaning as R or is a Cl atom, and $a$ has the value 0 to 1, characterised in that phospane compounds R$_3$P or quaternisation products thereof R$_3$PR'Cl are reacted at temperatures of 20° to 150° C with time tetrachloride.

In the preparation of the compounds of equation 3, the phosphine can also be reacted with other chlorine-donating oxidising agents, such as phosphorus(V) chloride, antimony(V) chloride, lead(IV) chloride or sulphuryl chloride or with elementary chlorine, before the reaction with tin(IV) chloride.

Examples of phosphane compounds for this synthesis are trimethylphosphine, triethylphosphine, tripropylphosphine, triisopropylphosphine, tributylphosphine, trihexylphosphine, triheptylphosphine, tricotylphosphine and tris-2-ethylhexylphosphine and quaternisazation products thereof with methyl chloride, ethyl chloride, propyl chloride, isopropyl chloride, butyl chloride, octyl chloride, 2-ethylhexylchloride and lauryl chloride, as well as dibutyldimethylphosphonium chloride and dioctyldimethylphosphonium chloride.

The compounds according to the invention are, in particular, outstanding catalysts for the preparation of organo-tin compounds from metallic tin or tin alloys of tin(II) chloride and organic halides, preferably for the preparation of dimethyl-tin dichloride from tin and methyl chloride.

Dimethyl-tin dichloride is an important intermediate product for methyl-tin stabilisers, which are employed for stabilising polymers containing chlorine. It is also used as a catalyst in the polyester condensation.

Only a few processes have been disclosed for the direct synthesis of dimethyl-tin dichloride from metallic tin and methyl chloride. The catalysts generally contain bromine compounds or iodine compounds or iodine in an elementary form.

GB-PS No. 1,275,843 describes organo-arsenic and organo-antimony compounds in combination with iodine as catalysts. The yields are low and are at most 46% in 5 hours. DT-AS No. 1,768,914 claims organo-antimony compounds as reaction accelerators. Iodine or iodine compounds or bromine compounds are always added. The best yields are about 90%, after a reaction time of 16 hours. DT-PS No. 1,217,951 mentions arsenic trihalides or antimony trihalides in combination with iodine compounds. Only syntheses of alkyl-tin halides having 4-12, particularly 8, C atoms in the hydrocarbon radical are carried out. In all these processes, undesired trigorgano-tin compounds are formed. None of these publications gives details concerning the return of the expensive iodine or bromine into the reaction cycle. Nor does one find statements concerning the life and re-usability of the catalysts employed, which is a matter of substantial importance for the profitability of a process.

These publications also display the disadvantage that they select, as accelerators of the reaction, compounds which take part in disproportionation reactions with organo-tin halides and thus contaminate the reaction products with undesired substances, which, with the toxicity of arsenic compounds is particular, requires care to be taken.

DT-AS No. 1,817,549 claims tetraalkylammonium iodides and tetraalkylphosphonium iodides as catalysts. Here also it is disadvantageous that, with the removal of the reaction products by distillation, the catalyst gradually becomes impoverished in the effective iodine compounds and thus loses activity. Although it is possible, in principle, to restore the initial effectiveness by further addition of iodine, such a step adds additional costs to the process. The other alternative consists of recycling the iodine removed. Although the Auslegeschrift which, in addition to long induction periods (8-10 hours), which cause great problems, also displays the disadvantage of considerable formation of triorgano-tin chloride (approx. 50%, see Example 26 which follows)

in the initial stage of the reaction, an effect which must not be ignored, particularly with the toxicity of trimethyl-tin compounds, does give details concerning the return of the iodine compounds removed by distillation, the method of extraction used for separating off the alkyl-tin chlorides is, however, too expensive for an industrial process.

It is a further disadvantage that all catalyst systems containing iodine rapidly deteriorate in effectiveness if they are not regenerated, that is to say either fresh addition of iodine or compounds thereof or recycling the alkyl-tin iodine compounds. The recurrent addition of alkyl iodides, which are not only expensive but also difficult to prepare, burdens a process with additional costs.

DT-OS No. 2,108,966 describes reactions of methyl chloride even in the absence of iodine or its compounds. Although the final yields are good, the reaction velocities are too low for industrial application.

It has now been found that the reaction of metallic tin or tin alloys with methyl chloride according to equation 1, in the presence of compounds of the formula I in which R, R' and a have the meaning indicated, leads to excellent yields accompaied by a high reaction velocity.

The tin can be employed here in any desired form, or example as tin dust, tin sponge, tin foil, powdered tin or tin bars or rods. Alloys of tin can also be used. On the laboratory scale it is preferable to use tin powder etched by means of hydrogen chloride, tin granules or freshly machined tin shavings and tin wire cut into short pieces having a clean and angular surface.

The particular advantages of using the complexes according to the invention are:

The starting materials for their manufacture are easily accessible, the complexes are formed very rapidly from the starting compounds in the presence or absence of solvents and it is not necessary to isolate them, the complexes themselves are also very suitable as a reaction medium, since they are liquid or molten under the reaction conditions specified and are not volatile, the complexes can also be employed in a diluted state, by virtue of their excellent solubility in customary solvents, they have a very good power of solvation for anhydrous tin(II) chloride, which is always formed in small quantities as a by-product and which they are capable of holding in solution during the reaction and of converting, together with methyl chloride, into monomethyl-tin trichloride, and owing to the absence of iodine or bromine or compounds thereof, corrsosion problems and the problem of returning these substances into the reaction cycle are eliminated — for example the expensive extraction of the laborious recovery from saponification liquors — and as a result effluent ballast material, which is harmful to the environment, is, at the same time, dispensed with, in spite of the absence of iodine and bromine, not only excellent yields but also outstanding reaction velocities are achieved, which are superior to all previously known systems, owing to the absence of recycling processes or the addition of fresh catalyst, the yield of products is constant and subject to no variations, when they are used, impoverishment of the catalyst and so a loss of activity cannot occur, and a better heat stability and substantially longer life of the catalyst and a cheapening of the synthesis are thus achieved, owing to the absence of compounds of extraneous elements there is not contamination of the reaction product by other, possible toxic, methyl-element chlorides, mixed halides are not formed, but instead pure chlorides which can be isolated particularly easily, the reaction starts at once and there is no induction period, as in the case of the other processes, virtually no trimethyl-tin chloride, which is undesirable owing to its toxicity, is formed in the course of the reaction, as a result of complex formation with tin tetrahchloride, no methyl-tin chloride is linked to the catalyst, which gives an additional increase in the yield, and under the reaction conditions selected, the catalysts are highly fluid and therefore pumpable, and, after a lengthy reaction time, do not begin to turn cloudy or tend to form a precipitate.

A further advantage of the complexes according to the invention consists of the fact that the exceptionally high reaction velocity makes it possible to employ for the industrial synthesis tin bars, which are commerically available and substantially cheaper, instead of finely divided tin (powder, shavings or granules).

FR-PS No. 1,446,994 describes, without quoting examples, inter alia phosphonium complexes with organo-tin halides $$R_a Sn\ X_{5-a}$$

wherein X is a chlorine or bromine atom, R is an organic group and $a$ is 1, 2 or 3. Compounds having $a = 0$, that is to say, for example, with tin(IV) chloride, are not mentioned.

The French patent specification, which in its 11 examples only describes reactions in the presence of bromine compounds, also mentions under No. 1 a heavy formation of triorgano-tin halide (53%). When using the catalyst systems according to the invention, trimethyl-tin cloride is virtually not formed.

The superiority of the catalysts according to the invention is demonstrated by Examples 1 to 10 which follow.

When using the compounds according to the invention as catalysts for the preparation of dimethyl-tin dichloride, it is not necessary to separate off the tin(II) chloride formed as a by-product according to equation 3, since it has virtually no influence on the course of the reaction, because it is reacted to form monomethyl-tin trichloride.

Compounds which are preferred for use as catalysts are:

[(C$_4$H$_9$)$_3$P]SnCl$_4$, [(C$_8$H$_{17}$)$_3$P]SnCl$_4$, [(C$_4$H$_9$)$_4$PCl]SnCl$_4$, [(i-C$_3$H$_7$)$_3$CH$_3$PCl]SnCl$_4$, [(C$_4$H$_9$)$_3$CH$_3$PCl]SnCl$_4$, [(C$_4$H$_9$)$_3$C$_8$H$_{17}$PCl]SnCl$_4$, [(C$_4$H$_9$)$_3$C$_{12}$H$_{25}$PCl]SnCl$_4$, [(C$_4$H$_9$)$_3$C$_{18}$H$_{37}$PCl]SnCl$_4$, [(C$_8$H$_{17}$)$_3$CH$_3$PCl]SnCl$_4$, [(C$_8$H$_{17}$)$_3$C$_2$H$_5$PCl]SnCl$_4$, [(C$_4$H$_9$)$_3$PCl$_2$]SnCl$_4$ and [(C$_8$Hl$_{17}$)$_3$PCl$_2$]SnCl$_4$.

In the preparation of dimethyl-tin dichloride, the compounds of formula I can be employed in fairly large quantities as a reaction medium, without a solvent, or can be employed diluted, in the presence of solvents, a melt or a liquid system being present in the first case and, when used only as a catayst, 0.005 to 0.05 mol per mol of tin being preferably employed. It is desirable and advantageous to operate with a solvent, because only minor amounts of the catalysts of formula I must be used in this case, which is more economic. Generally it is possible to remove the formed dimelhyltin by dichloride distillation and to use again for more times the residue consisting of the catalyst and the solvent. A further advantage is the lower viscosity of the reaction mixture which can be cycled much better in a continuous process in suitable apparatus.

If solvents are used, cyclic sulphones, such as methylsulpholanes and chlorosulpholanes, or cyclic carbonic acid esters or thio-homologues thereof, such as 1,3-butylene carbonate and ethylene monothio-, dithio- or trithio-carbonate, have proved advantageous, because, in contrast with other solvents, they virtually do not decrease the yields and the reaction velocities. Tetramethylenesulphone or propylene carbonate are preferred. Further typical examples are:

Tetramethylenesulfone (Sulfolan®), butadienesulfone (sulfolen®), 3-methylsulfone, 2,4-dimethylsulfone, 2,3-dimethylsulfone, 3-chlorosulfone, 2,3-dichlorsulfone, 3-hydroxysulfone, 3-chloro-4-hydroxysulfone, 3-dimethylaminosulfone, 3-acetoxysulfone, di-3-sulfonyl ether, methoxysulfone, 3,4-dimethoxysulfone, isopropoxysulfone, tetrahydro-1-thiapyrane-1,1-dioxide, tetrahydrotetramethyl-1-thiapyrane-1,1-dioxide, thiacane-1,1-dioxide, thianane-1,1dioxide.

The range of temperature and pressure for the reaction is between 100° and 300° and between 0 and 150 atmospheres gauge. It is preferable to operate between 150° and 180° and, for reasons of apparatus, at a pressure of 0 to 10 atmospheres gauge, especially at normal pressure. If operations are carrried out with tin melts, the tin melting point should be exceeded by about 10° to 20°. The range between 200° and the melting point has proved less advantageous, because the active surface of the tin is constantly decreased as a result of a slow sintering process of the latter, which leads to a decrease in the reaction velocity.

A possible agglomeration of tin particles during the reaction can be prevented by the addition of a little red phosphorous or elementary sulphur.

The dimethyl-tin compounds can be isolated from the reaction mixture by saponification. Thus, on treatment with aqueous alkali, dimethyl-tin oxide is produced in an insoluble form, the catalyst constituent tin(IV) going into solution as a stannate. The dimethyl-tin oxide can optionally be re-converted into the chloride in a customary manner.

It is preferable, however, to separate continuously by means of distillation or sublimation. In a particularly preferred embodiment, the distillation residue is used for further reactions without working up or returning reaction products or adding new catalyst constituents. This offers the possibility of continuously adding tin and methyl chloride in a continuous process, diverting a part of the reaction solution, distilling the reaction product off from the latter and recycling the residue into the process.

EXAMPLE 1

A stirred autoclave is charged with 10 parts of the complex

90 parts of tetramethylenesulphone, 50 parts of methyl chloride and 50 parts of tin shavings. After being reacted for 6 hours at 180° C and about 135 atmospheres gauge, 88% of the tin have reacted. After working up by distillation, 79 parts of pure dimethyl-tin dichloride (851 % of theory ( are obtained, which corresponds to 13.2 parts/hour.

EXAMPLE 2

50 parts of tin shavings are allowed to react with methyl chloride at normal pressure in the presence of 14 parts of the complex

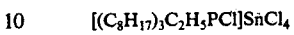

in 86 parts of propylene carbonate. After 8 hours at 170° C, 92% of the tin have reacted. Pure dimethyl-tin dichloride is obtained by distillation in a yield of 88%, which corresponds to 10.2 parts/hour.

EXAMPLE 3

In 50 parts of a solution consisting of 5 parts of [(C₄H₉)₄PCl]SnCl₄ and
45 parts of Sulfolan methyl chloride is reacted at 170° C under normal pressure, with stirring and reflux cooling, with 85 parts of tin powder. The formed dimethyltin dichloride is removed from the reaction system on average every 6–8 hours by distillation under vacuum, with an addition being made from time to time of fresh tin.

After 8 hours reaction time, the dimethyltin dichloride yield is 92%, relative to the tin used.

The following Table shows the pattern of yield obtained:

| Fraction | Reaction time h | Yield Parts | Parts / h |
|---|---|---|---|
| I |  | 130 | 2860 | 22 |
| II | further | 50 | 1220 | 24 |
| III | further | 35 | 650 | 19 |
| IV | further | 40 | 620 | 16 |

The employed catalyst system is thermally very stable; the average yield after a total reaction time 255 hours is still 21 parts per hour.

By means of complexometrical (monomethyltin trichloride) and gas-chromatographical (trimethyltin monochloride)l determination, in all 4 fractions, the content of CH₃SnCl and (CH₃)₃SnCl as tin was analysed as being <0.2% tin.

EXAMPLE 4

In 100 parts of a solution consisting of 25 parts of [(C₄H₉)₃CH₃PCl]SnCl₄ and
75 parts of Sulfolan 100 parts of tin powder are reacted at 180° C, with stirring and reflux cooling, with methyl chloride gas. The formed dimethyltin dichloride is removed every 5-7 hours by distillation under vacuum. The further addition of fresh tin is made successively.

96% of the added tin has been reacted after 5 hours. The following Table shows the course of reaction:

| Fraction | Reaction time h | Yield Parts | Parts / h |
|---|---|---|---|
| I | 35 | 1220 | 35 |

-continued

| Fraction | Reaction time h | Yield Parts | Parts / h |
|---|---|---|---|
| II | further 80 | 2780 | 35 |

The yield during 115 hours is thus 35 parts per hour.

EXAMPLE 5

In 100 parts of a solution consisting of 15 parts of $[(C_4H_9)_3P]SnCl_4$ and
85 parts of propylene carbonate 100 parts of tin chips are reacted at 180° C with gaseous methyl chloride. The formed dimethyltin dichloride is removed from the melt every 6-8 hours by means of evacuation. Fresh tin chips are added from time to time. After 15 hours reaction time, 178 parts of the total added 185 parts of tin have reacted, which corresponds to a tin conversion of 97%.

The following Table shows the pattern of yield:

| Fraction | Reaction time h | Yield Parts | Parts / h |
|---|---|---|---|
| I |  50 | 1020 | 20 |
| II | further 25 | 510 | 20 |
| III | further 35 | 740 | 21 |
| IV | further 50 | 1055 | 21 |

The rate of reaction is practically constant. After a total reaction time of 160 hours, the reaction system still shows no formation of precipitate.

The fractions II-IV give the following analysis results:

| Fraction | Tin % | Chlorine % | % Tin as $CH_3SnCl_3$ |
|---|---|---|---|
| II | 55.0 | 32.4 | 0.3 |
| III | 54.8 | 32.9 | 0.2 |
| IV | 54.7 | 31.9 | 0.2 |

These results show that the dimethyltin dichloride distilled off has a purity of at least 99%.

EXAMPLE 6

An autoclave with stirrer is charged with 10 parts of the complex $[(i-C_3H_7)_3CH_3PCl]SnCl_4$ and
90 parts of Sulfolan, as well as
50 parts of methyl chloride and
50 parts of tin chips.

After 6 hours' reaction at 180° C under about 135 atm., the amount of tin reacted is 88%. After processing by distillation, there are obtained 79 parts of pure dimethyltin dichloride (85% of theory), which corresponds to 13.2 parts/hour.

EXAMPLE 7

In the presence of 14 parts of the complex $[(C_8H_{17})_3C_2H_5PCl]SnCl_4$ and
86 parts of propylene carbonate, 50 parts of tin chips are reacted at normal pressure with methyl chloride. 92% of the tin has reacted after 8 hours at 170° C. By distillation there is obtained pure dimethyltin dichloride in a yield of 88%, which corresponds to 10.2 parts/hour.

EXAMPLE 8

19 parts of tributylphosphine are reacted for 2 hours at 120° C, with stirring and reflux cooling, with 50 parts of tin(IV)-chloride to the complex $[(C_4H_9)_3PCl_2]SnCl_4$.

Through the unprocessed melt there is passed at 170° C for 3 hours a vigorous stream of methyl chloride. There is subsequently distilled off at 160° C, in a water-jet vacuum, 21 g of monomethyltin trichloride at a purity of 97%.

After the addition of 100 parts of Sulfolan and 100 parts of tin powder, the mixture is treated with methyl chloride gas. Distillation and the fresh addition of tin are carried out as in the other tests.

After a reaction time of 8 hours, 88% of the added tin has reacted.

The following Table shows the pattern of yield:

| Fraction | Reaction time h | Yield Parts | Parts / h |
|---|---|---|---|
| I |  30 | 630 | 21 |
| II | further 50 | 50 | 23 |

The melt after a reaction time of 80 hours shows no signs of turbidity. The mean yield is 22 parts/hour.

An analysis of samples taken gives the following material balance:

| Reaction time h | Yield | Composition $(CH_3)_2SnCl_2$ | $CH_3SnCl_3$ | $(CH_3)_3SnCl$ | Chlorine content theor. | found |
|---|---|---|---|---|---|---|
| 7 | 145 | 82.3 | 14.9 | 0.2 | 32.2 | 32.2 |
| further 73 | 1610 | 96.7 | 1.7 | 0.2 | 31.8 | 31.8 |

At 0.2% the proportion of $(CH_3)_3SnCl$ is extraordinarily low.

EXAMPLE 9 (comparison Example)

In 40 parts of a melt of the complex $[(C_4H_9)_4PCl]SnCl_4$, 85 parts of tin powder are reacted at 170° C at normal pressure, with stirring and reflux cooling, with methyl chloride. The formed dimethyltin dichloride is removed from the reaction system on average every 2 hours by distillation in a water-jet vacuum, with fresh tin being added from time to time.

After a reaction time of 8 hours, the yield of dimethyltin dichloride is 93%, relative to the tin used.

A comparison with Example 3 shows that, within the error of measurement, there is practically no decline in the yield of dimethyltin dichloride (see in this respect also Examples 1–5, 11, 14–16, 24 and 25 of U.S. Pat. No. 3,901,824, in which likewise catalyst concentrations are used).

EXAMPLE 10 (comparison Example)

5 parts of tin sheet and
0.3 part of [(C$_4$H$_9$)$_3$CH$_3$PCl]SnCl$_4$ and
100 parts of /Sulfolan
are heated with stirring to 180° C. Methyl chloride is passed through the reaction mixture until the whole amount of tin is reacted. The time taken for the complete conversion of the tin is determined.

The procedure is performed analogously in the case of the other systems given below, whereby conventional solvents are used in place of Sulfolan.

| Reaction Medium | Pressure (atm) | Time to obtain complete reaction of the tin in hours |
|---|---|---|
| Sulfolan | 1 | 6 |
| Propylene carbonate | 1 | 8 |
| Di-n-butyl ether | 4 | 35 |
| Cyclohexylacetate | 1 | 70 |
| Di-n-octyl ether | 1 | 39 |
| Triethylene glycoldimethyl ether | 1 | 32 |
| Diethyleneglycoldimethyl ether | 1 | 46 |
| Tetrahydrofuran | 6 | 41 |
| Isooctane | 3 | after 50 hours not tin-consumption |

We claim:

1. An improved process for the manufacture of dimethyl-tin dichloride by the reaction of metallic tin or tin alloys with methyl chloride at 100° to 300° under a pressure of 0 to 150 atmospheres gauge in the presence of at least one compound of formula I $$[R_3P(R'Cl)_a]SnCl_4 \qquad (I)$$

in which R is a straight or branched chain alkyl of 1 to 18 carbon atoms, R' has the same meaning as R or is a Cl atom and $a$ has the value 0 or 1, wherein the improvement comprises
   carrying out the reaction in the presence of a solvent selected from the group consisting of cyclic sulfones, cyclic carbonates and cyclic thiocarbonates.

2. A process according to claim 1, characterized in that R is an alkyl group having 1 to 12 C atoms, R' has the same meaning as R or is a Cl atom, and $a$ has the value 0 or 1.

3. A process according to claim 1, characterized in that compounds of the formula I are used as catalysts in quantities of 0.005 to 0.05 mol, relative to the tin.

4. A process according to claim 1, characterized in that tetramethylenesulphone or propylene carbonate is used as the solvent.

5. A process according to claim 1, characterized in that the dimethyl-tin dichloride formed is continuously removed from the reaction by sublimation or distillation.

6. A process according to claim 1, characterized by the reaction being at 150° to 180° C.

7. A process according to claim 1, characterized in that the reaction is carried out at a pressure of 0 to 10 atmospheres gauge.

8. A process according to claim 1, characterized by a continuous operation of the process, the starting materials being continuously added as they are consumed, a part of the reaction solution being diverted, the reaction product being removed by distillation from the latter and the residue being returned to the process.

* * * * *